United States Patent
Baker et al.

(10) Patent No.: US 7,381,740 B2
(45) Date of Patent: Jun. 3, 2008

(54) MELATONIN ANALOGUE PRODRUGS

(75) Inventors: Max T. Baker, Iowa City, IA (US); Mohamed Naguib Attala, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 383 days.

(21) Appl. No.: 10/973,692

(22) Filed: Oct. 26, 2004

(65) Prior Publication Data

US 2005/0154047 A1 Jul. 14, 2005

Related U.S. Application Data

(60) Division of application No. 10/078,643, filed on Feb. 19, 2002, now Pat. No. 6,638,966, which is a continuation-in-part of application No. 09/927,687, filed on Aug. 10, 2001, now Pat. No. 6,552,064.

(60) Provisional application No. 60/514,952, filed on Oct. 27, 2003, provisional application No. 60/233,785, filed on Sep. 19, 2000.

(51) Int. Cl.
A61K 31/405 (2006.01)
(52) U.S. Cl. .................................. 514/415
(58) Field of Classification Search ............... 514/419, 514/415
See application file for complete search history.

(56) References Cited

U.S. PATENT DOCUMENTS

| 5,196,435 | A | | 3/1993 | Clemens et al. |
| 5,932,608 | A | * | 8/1999 | Nguyen et al. ............ 514/415 |
| 6,004,991 | A | | 12/1999 | Fourtillan et al. |
| 6,071,928 | A | | 6/2000 | Curtis |

FOREIGN PATENT DOCUMENTS

| EP | 0 513 702 A2 | 11/1992 |
| EP | 0 867 181 A1 | 9/1998 |

OTHER PUBLICATIONS

Beers, M.H., "The Merck Manual", 1999, Merck Research Laboratories, Rahway, NJ, XP002222217, p. 1413, paragraph 2.

Chaiyakul, "Melatonin Dose-Dependently inhibits Ketamine-Induced Anesthesia in Rats", *Society for Neuroscience Abstracts*, vol. 25, No. 1-2, 1999, p. 922 XP001109176, 19th Annual Meeting of the Society for Neuroscience; Miami Beach, Florida, USA, Oct. 23-28, 1999, ISSN:0190-5295, abstract.

Dubocovich et al., CA111:153621, WO 8901472, Feb. 23, 1989, abstract.

Mallo et al., "Effects of a four-day nocturnal melatonin treatment on the 24 h plasma melatonin, cortisol and prolectin profiles in humans" *Acta Endocrinol*, 1988 Dec. 119(4), 474-80, abstract.

Naguib M et al., "Premedication with melatonin: A double-blind, placebo-controlled comparison with midazolam", *Brittish Journal of Anaesthesia*, vol. 92, No. 6, Jun. 1999, pp. 875-880, XP008010666 ISSN: 0007-0912.

Naguib M et al., "The comparative dose-response effects of melatonin and midazolam for premedication of adult patients: A double-blindfed, placebo-controlled study," *Anesthesia& Analgesla*, vol. 91, No. 2, Aug. 2000, pp. 473-479, XP008010667, ISSN: 0003-2999 abstract.

Vijayalaxmi et al., "Melatonin and protection from whole-body irradiation: survival studies in mice", *Mutation Research*, Netherlands Mar. 10, 1999, vol. 425. No. 1, Mar. 10, 1999, pp. 21-27, XP002222723, ISSN: 0027-5107, abstract.

* cited by examiner

*Primary Examiner*—Ardin Marschel
*Assistant Examiner*—James D Anderson
(74) *Attorney, Agent, or Firm*—McKee, Voorhees & Sease, P.L.C.

(57) ABSTRACT

Disclosed are compounds that can serve as melatonin analogue prodrugs and that are soluble in aqueous solvents. Melatonin or melatonin analogues having modifications to the indole moiety are coupled to a tertiary amine to form a quaternary amine such that there is a saturated two-carbon linkage between the carbonyl of the melatonin structure and the amine nitrogen. This structure is stable in acidic environments, but is unstable at basic or neutral pH. Therefore, these melatonin analogue prodrugs are stable in a vial at acidic pH, but will breakdown upon injection into the body to liberate the melatonin analogue and the tertiary amine, which is nontoxic. The melatonin analogue being not modified on the indole moiety exerts similar pharmacological properties as melatonin: antioxidation, sedation and anesthesia.

12 Claims, No Drawings

MELATONIN ANALOGUE PRODRUGS

CROSS-REFERENCE TO RELATED APPLICATIONS

This application claims the benefit of the filing date of Provisional Application Ser. No. 60/514,952 which claims priority to prior U.S. application Ser. No. 10/078,643 filed Feb. 19, 2002, now U.S. Pat. No. 6,638,966, which is a CIP of Ser. No. 09/927,687 filed Aug. 10, 2001, now U.S. Pat. No. 6,552,064, which was a nonprovisional application of 60/233,785 filed Sep. 19, 2000 herein incorporated by reference in its entirety. See also U.S. application Ser. No. 10/420,242 filed Apr. 22, 2003 which is a Divisional of Ser. No. 10/078,643.

BACKGROUND OF THE INVENTION

In the medical field there is a continuing need for new compounds having demonstrated use for inducing anesthesia. It is not only important to induce beneficial anesthesia, but it must be done in a manner that limits toxicity to patients, and as well, minimizes what is known as "anesthesia hangover".

The pineal hormone melatonin (N-acetyl-5-c) has several putative functions, including regulation of circadian rhythms, regulation of the reproductive axis and antioxidant activity. Autoradiographic studies and receptor assays have demonstrated the presence of melatonin receptors in various regions of the central nervous system and in other tissues in humans.

Exogenous administration of melatonin has been found by several investigators to facilitate sleep onset and improve quality of sleep. Available data suggest that the sleep-inducing properties of melatonin may differ from those of benzodiazepines. Benzodiazepines decrease duration of REM sleep after single administration of a high dose or long-term administration of low dose. Benzodiazepines also reduce slow-wave sleep, thus negatively influencing sleep quality. In contrast, a single low dose of melatonin produced no suppression of REM sleep. Furthermore, unlike benzodiazepines, melatonin does not induce "hangover" effects.

In a previous publication of one of the inventors, British Journal of Anesthesia 82(6): 875-80(1999), low-level dosing of oral melatonin in a sublingual fashion was demonstrated as an effective pre-medication, prior to administering a general anesthetic. Patients who were administered such low-level doses sublingually had a significant decrease in anxiety levels and an increase in levels of sedation before operation. However, as pointed out in that article, the use of melatonin in anesthesia had as of then never been evaluated properly, and to the inventor's present knowledge it has never been used as a general anesthetic prior to this series of applications.

The invention of our U.S. Pat. No. 6,522,064 had as its primary objective the development of pineal hormone melatonin (N-acetyl-5-methoxytryptamine) or its biologically active analogues as a general anesthetic which can be used without any significant anesthetic hangover. The continuing need in the art for meeting that objective was readily apparent.

With reference to the continuing need referred to above, applicants continued to work with melatonin and its analogues to derive improved compounds which may be used for anesthetic effect generally and in small doses for hypnotic effect sedation or even sleep inducement. This continuing work evolved into the discovery that 2-trihalo methyl melatonins and in particular the 2-trifluoromethylmelatonin are substantially more active in anesthetic effect than melatonin itself. The result of this increased activity meant that the compounds may be used in larger doses for general anesthesia, but in smaller doses for hypnotic effect and sedation and sleep effect.

Further discoveries since the filing of the original application have revealed a particularly effective pharmaceutical carrier for melatonin, melatonin analogues and the improved derivatives of the present invention. The carrier allows dissolving and high concentrations of melatonin or its analogues. The preferred carrier is comprised of one volume of 1-methyl-2-pyrrolidinone, one volume of propylene glycol and two volumes of water. It goes without saying that the volumetric ratios of these carrier solvents may be varied somewhat, depending upon the circumstances. These discoveries resulted in our U.S. Pat. No. 6,638,966.

Because melatonin and the melatonin analogues of our previous patents are somewhat difficultly soluble in aqueous vehicles, the Applicants have continued their efforts to find active analogues which could be administered with aqueous vehicles.

Disclosed here are prodrugs of melatonin analogues which can be administered preferentially in aqueous vehicles. Melatonin is a water-insoluble compound that cannot be administered to patients by injection using an aqueous vehicle. Furthermore, melatonin can not be formulated into an organic solvent that is free of side effects. For example, organic solvents such as ethanol, N-methyl-pyrrolidione, ethyl acetate, tetrahydrofuran, and propylene glycol, will solublize melatonin; however, these solvents are either toxic to the patient, have undesirable side-effects, or they are not approved for administration to humans by parenteral administration. Melatonin also cannot be administered in an oil-in-water emulsion because it is poorly soluble in oils that can be made into oil-in-water emulsions, such as soybean, safflower, or olive oil.

It is therefore desired to have a compound, which exerts the beneficial effects of melatonin including anti-oxidation, sedation, anesthesia, protection of organs to chemical, infectious and cardiovascular damage, and can be administered in a water-based or aqueous vehicle. This invention fulfills this desire or need.

BRIEF SUMMARY OF THE INVENTION

Disclosed are compounds that can serve as melatonin analogue prodrugs and that are soluble in aqueous solvents. Melatonin or melatonin analogues having modifications to the indole moiety are coupled to a tertiary amine to form a quaternary amine such that there is a saturated two-carbon linkage between the carbonyl of the melatonin structure and the amine nitrogen. This structure is stable in acidic environments, but is unstable at basic or neutral pH. Therefore, these melatonin analogue prodrugs are stable in a vial at acidic pH, but will breakdown upon injection into the body to liberate the melatonin analogue and the tertiary amine, which is nontoxic. The melatonin analogue being not modified on the indole moiety exerts similar pharmacological properties as melatonin: antioxidation, sedation and anesthesia.

DETAILED DESCRIPTION OF A PREFERRED EMBODIMENT

N-acetyl-5-methoxytryptamine (melatonin) is synthesized mainly by the pineal gland, and to a lesser extent by extra pineal tissues such as the retina, harderian gland, and gastrointestinal tract. Melatonin has the following structure:

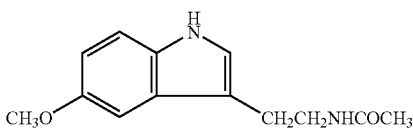

As seen, the chemical formula for melatonin is N-acetyl-5-methoxytryptamine. From time to time in the specification applicant uses the term "biologically active analogues". As used herein, this phrase refers to the precise compound itself and other compounds having the same general structure, but only differing in minor moieties, and therefore still having the same biological activity of anesthetic-inducing effectiveness. The biologically active compound melatonin, may be derived or extracted from the pineal gland, or it can be synthesized from 5-Methoxyindol as a starting material by known routes, Szrnuszkovicz et al., J. Org. Chem. 25, 857 (1960). Biochemical role of melatonin: Chem. & Eng. News 45, 40 (May 1, 1967).

Chemically, the word description of the above is illustrated by the following schematic:

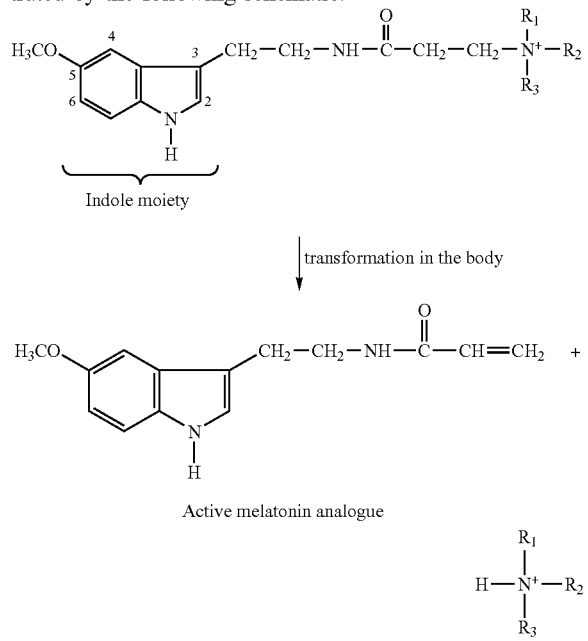

$R_1$, $R_2$ and $R_3$ can independently be any hydrocarbon moiety which upon hydrolysis provides a non toxic tertiary amine including for example alkyl, cycloalkyl, haloalkyl, phenyl, or aromatic groups, but preferably $R_1$, $R_2$ and $R_3$ are short chain, i.e., $C_1$ to $C_8$, most preferably $C_1$ to $C_4$ alkyl. $R_1$, $R_2$ and $R_3$ may also contain multiple substituent groups including in addition, alkoxy, carboxylic acid or ester groups, and may have up to $C_{20}$.

The indole structure of the melatonin analogue may be substituted at the 2-position with substituents including bromine, chlorine, chlorine, fluorine, phenyl, 4-fluorophenyl, 4-bromophenyl, 4-trifluorophenyl or other related groups (see our U.S. Pat. No. 6,638,966).

The anesthetic active, i.e., the prodrug of N-acetyl-5-methoxytryptamine (melatonin), or its biologically active analogues, can be administered with traditionally acceptable pharmaceutical carriers. Examples include Intralipid®, Cyclodextrin, and others, some of which are briefly hereinafter described. However, there is no need for detailed description of suitable anesthetic carriers because they are so well known in the industry.

Intravenous administration of the prodrug in an aqueous solvent system results in a rapid increase in blood melatonin concentrations in rats that are suitable to cause an unexpected anesthetic effect without causing toxic side effects.

Formulations containing the prodrugs of melatonin analogues that consist of melatonin or its analogues in water can be used. Derivatives or analogues of prodrugs of melatonin, such as 2-bromomelatonin and 2-phenylmelatonin may be administered in solvents described above.

The composition may be administered by conventional administration methods for anesthetics, i.e., oral administration, nasal respiratory administration, bolus injection, intravenous administration by repeated doses or by continuous infusion, rectal, vaginal, sublingual, cutaneous and slow release routes. It may be, and often is preferred, that it be administered in two or more ways, such as by bolus injection followed by continuous intravenous administration.

The liquid forms in which the novel compositions of the present invention may be incorporated for administration orally or by injection include aqueous solutions, suitably flavored syrups, and aqueous suspensions. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin and these pay be used.

Compositions for inhalation or insufflation include solutions and suspensions in pharmaceutically acceptable, aqueous or organic solvents, or mixtures thereof, and powders. The liquid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device, or the nebulising device may be attached to a face mask, tent or intermittent positive pressure breathing machine. Solution, suspension or powder compositions may be administered, preferably orally or nasally, from devices which deliver the formulation in an appropriate manner.

The anesthetic may be used alone or often in combination with other anesthetics simultaneously administered. Put another way, it will be appreciated that when using any combination described herein, both the compound of melatonin or its analogue and the other active agent(s) can be administered to a patient, within a reasonable period of time. It may indeed act synergistically with other anesthetic drugs. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active compound may be administered as a tablet and then, within a reasonable period of time, the second active component may be administered either as an oral dosage form such as a tablet or a fast-dissolving oral dosage form. By a "fast dissolving oral formulation" is meant, an oral delivery form which, when placed on the tongue of a patient, dissolves within about 10 seconds.

The dosage will vary depending upon the deepness of the anesthesia desired, but based upon limited studies to date, it is believed that the dosage most effective will be within the range of 0.001 mg/kg of body weight to about 500 mg/kg of body weight, more predictably preferred is the range of 5 mg/kg of body weight to about 350 mg/kg of body weight.

The synthesis of the melatonin analogue prodrugs may be summarized by the following reaction scheme.

Melatonin Analogue Prodrug Synthesis
A Pathway for the Synthesis of a Melatonin Analogue Prodrug
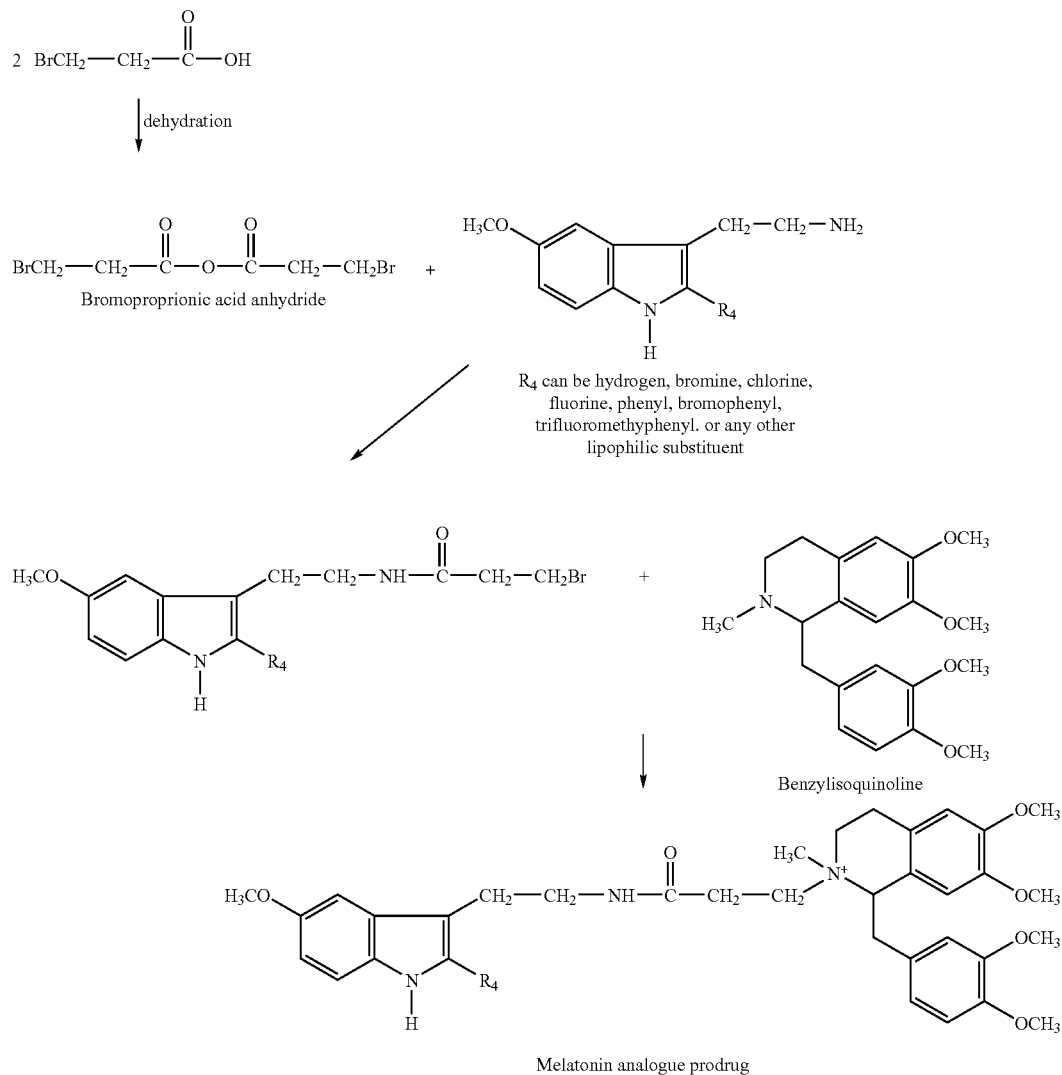
Prodrug shown above, upon hydrolysis will yield the melatonin analogue and a tertiary amine.
Another example of a melatonin analogue prodrug is illustrated below.
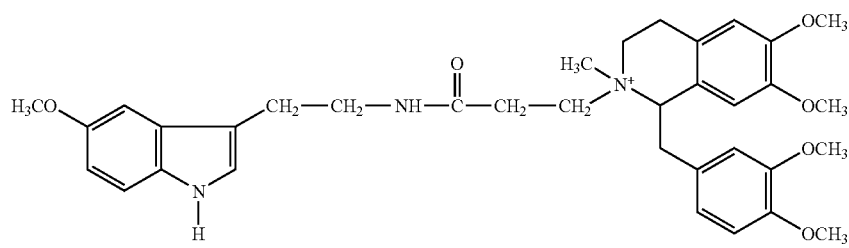

Example of a Melatonin Analogue Prodrug

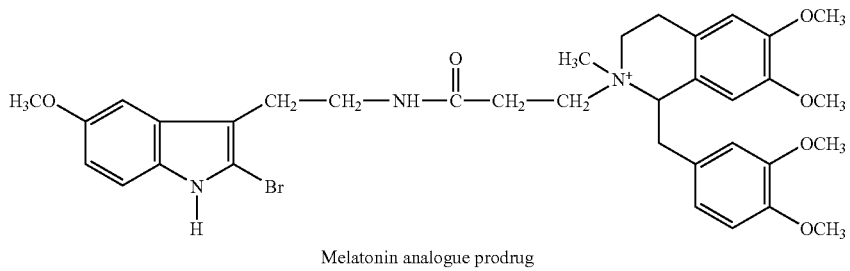

Melatonin analogue prodrug

↓ Transformation in the body

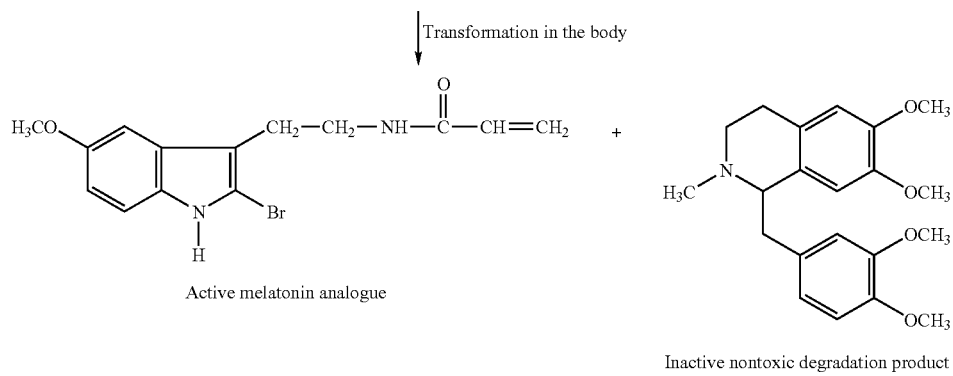

Active melatonin analogue + Inactive nontoxic degradation product

From the above illustrations, it can be seen that active melatonin analogue prodrugs, transformable into the active melatonin analogue within the body are provided. These are aqueous carrier soluble and as such have ease of administration and will break down upon injection into the body to liberate the melatonin analogue and a non toxic tertiary amine.

What is claimed is:

1. A composition comprising:

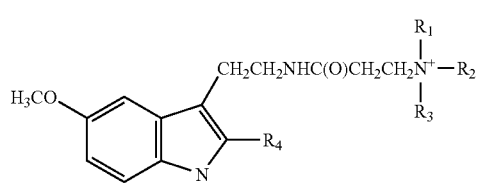

where $R_4$ is selected from the group consisting of hydrogen, fluorine, chlorine, bromine, iodine, phenyl, 4-fluorophenyl, 4-bromophenyl, 4-(trifluoromethyl)phenyl and where $R_1$, $R_2$ and $R_3$ are independently chosen from the group consisting of hydrogen, alkyl, cycloalkyl, haloalkyl, phenyl, alkoxyalkyl, carboxyalkyl, alkoxycycloalkyl, carboxycycloalkyl, alkoxyhaloalkyl, carboxyhaloalkyl, alkoxyphenyl, carboxyphenyl, alkylesteralkyl, cycloakylesteralkyl, alkylestercycloalkyl, alkylesterphenyl, phenylalkylester and alkoxyarylalkyl, alcohols, and an aqueous pharmaceutical carrier.

2. The composition of claim 1 wherein $R_1$, $R_2$ and $R_3$ are from $C_1$ to $C_{20}$ moieties.

3. The composition of claim 2 wherein $R_1$, $R_2$ and $R_3$ are $C_1$ to $C_8$ moieties.

4. The composition of claim 3 wherein $R_1$, $R_2$ and $R_3$ are $C_1$ to $C_4$ moieties.

5. A composition comprising:

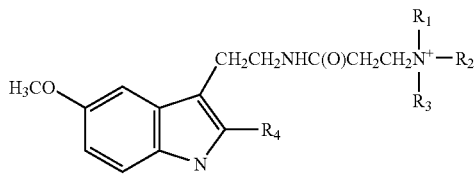

where $R_4$ is selected from the group consisting of hydrogen, fluorine, chlorine, bromine, iodine, phenyl, 4-fluorophenyl, 4-bromophenyl, 4-(trifluoromethyl)phenyl and where $R_1$, $R_2$ and $R_3$ are independently chosen from the group consisting of hydrogen, alkyl, cycloalkyl, haloalkyl, phenyl, alkoxyalkyl, carboxyalkyl, alkoxycycloalkyl, carboxycycloalkyl, alkoxyhaloalkyl, carboxyhaloalkyl, alkoxyphenyl, carboxyphenyl, alkylesteralkyl, cycloakylesteralkyl, alkylestercycloalkyl, alkylesterphenyl, phenylalkylester and alkoxyarylalkyl, alcohols.

6. The composition of claim 5 wherein $R_1$, $R_2$ and $R_3$ are from $C_1$ to $C_{20}$ moieties.

7. The composition of claim 6 wherein $R_1$, $R_2$ and $R_3$ are $C_1$ to $C_8$ moieties.

8. The composition of claim 7 wherein $R_1$, $R_2$ and $R_3$ are $C_1$ to $C_4$ moieties.

9. A method of producing a pharmaceutically active melatonin analogue in situ after delivery to a patient, consisting essentially of providing a soluble melatonin analogue prodrug of the formula

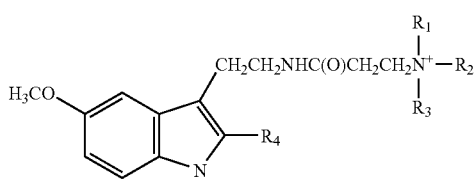

where $R_4$ is selected from the group consisting of hydrogen, fluorine, chlorine, bromine, iodine, phenyl, 4-fluorophenyl, 4-bromophenyl, 4-(trifluoromethyl)phenyl and where $R_1$, $R_2$ and $R_3$ are independently chosen from the group consisting of hydrogen, alkyl, cycloalkyl, haloalkyl, phenyl, alkoxyalkyl, carboxyalkyl, alkoxycycloalkyl, carboxycycloalkyl, alkoxyhaloalkyl, carboxyhaloalkyl, alkoxyphenyl, carboxyphenyl, alkylesteralkyl, cycloakylesteralkyl, alkylestercyloalkyl, alkylesterphenyl, phenylalkylester, and alkoxyarylalkyl, alcohols, in an aqueous pharmaceutical carrier;

administering it to a patient in need thereof, and waiting for the melatonin analogue prodrug to hydrolyze in a neutral or basic environment in the body so that the melatonin analogue is liberated to provide its desired effect.

10. The method of claim 9 wherein $R_1$, $R_2$ and $R_3$ are from $C_1$ to $C_{20}$ moieties.

11. The method of claim 10 wherein $R_1$, $R_2$ and $R_3$ are $C_1$ to $C_8$ moieties.

12. The method of claim 11 wherein $R_1$, $R_2$ and $R_3$ are $C_1$ to $C_4$ moieties.

\* \* \* \* \*